(12) United States Patent
Minagawa et al.

(10) Patent No.: US 10,406,149 B2
(45) Date of Patent: *Sep. 10, 2019

(54) AQUEOUS LIQUID FORMULATION

(71) Applicant: KYORIN PHARMACEUTICAL CO., LTD., Tokyo (JP)

(72) Inventors: Wataru Minagawa, Tochigi (JP); Hitoshi Kozuka, Tochigi (JP); Mizuho Shibata, Tochigi (JP); Takahiro Goto, Tochigi (JP); Chifuyu Toriumi, Tochigi (JP); Norihiro Kanayama, Tochigi (JP)

(73) Assignee: KYORIN PHARMACEUTICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/578,764

(22) PCT Filed: Jun. 2, 2016

(86) PCT No.: PCT/JP2016/066411
§ 371 (c)(1),
(2) Date: Dec. 1, 2017

(87) PCT Pub. No.: WO2016/195021
PCT Pub. Date: Dec. 8, 2016

(65) Prior Publication Data
US 2018/0147199 A1 May 31, 2018

(30) Foreign Application Priority Data

Jun. 2, 2015 (JP) ................................. 2015-111864

(51) Int. Cl.
*A61K 31/4709* (2006.01)
*A61K 47/02* (2006.01)
*A61K 9/08* (2006.01)
*A61P 31/04* (2006.01)

(52) U.S. Cl.
CPC ............ *A61K 31/4709* (2013.01); *A61K 9/08* (2013.01); *A61K 47/02* (2013.01); *A61P 31/04* (2018.01)

(58) Field of Classification Search
CPC ................................................ A61K 31/4709
USPC ........................................................ 514/312
See application file for complete search history.

(56) References Cited

U.S. PATENT DOCUMENTS

| 5,304,559 | A | 4/1994 | Rozier |
| 5,334,589 | A | 8/1994 | Al-Razzak |
| 5,811,130 | A | 9/1998 | Boettner et al. |
| 6,288,080 | B1 | 9/2001 | Barsuhn et al. |
| 2004/0082593 | A1 | 4/2004 | Sommermeyer et al. |
| 2006/0281779 | A1 | 12/2006 | Asahina et al. |
| 2007/0197548 | A1 | 8/2007 | Murthy |
| 2009/0117205 | A1 | 5/2009 | Yano et al. |
| 2014/0288310 | A1 | 9/2014 | Araya et al. |
| 2016/0067185 | A1 | 3/2016 | Uchida et al. |
| 2016/0074330 | A1 | 3/2016 | Uchida et al. |

FOREIGN PATENT DOCUMENTS

| EP | 3 305 294 | 4/2018 |
| EP | 3 305 295 | 4/2018 |
| JP | 63-188626 | 8/1988 |
| JP | 2-264724 | 10/1990 |
| JP | 4-230631 | 8/1992 |
| JP | 2003-226643 | 8/2003 |
| JP | 2004-509921 | 4/2004 |
| WO | 91/09525 | 7/1991 |
| WO | 97/23217 | 7/1997 |
| WO | 99/29322 | 6/1999 |
| WO | 2005/026147 | 3/2005 |
| WO | 2006/004028 | 1/2006 |
| WO | 2014/174846 | 10/2014 |
| WO | 2014/174847 | 10/2014 |
| WO | 2014/174848 | 10/2014 |

OTHER PUBLICATIONS

Alarcon et al., "Antimicrobial properties, etc.," Magnesium Research: 27 (2) 57-68. (Year: 2014).*
International Search Report dated Jul. 12, 2016 in International (PCT) Application No. PCT/JP2016/066411.
International Preliminary Report on Patentability dated Dec. 5, 2017 in International (PCT) Application No. PCT/JP2016/066411.
Extended European Search Report dated Jan. 18, 2019 in corresponding European Application No. 16803455.1.

* cited by examiner

*Primary Examiner* — Patricia L Morris
(74) *Attorney, Agent, or Firm* — Wenderoth, Lind & Ponack, L.L.P.

(57) ABSTRACT

A novel technique with which it is possible to suppress chemical degradation of a compound represented by general formula (1) or a salt thereof in an aqueous liquid formulation containing a compound represented by general formula (1) or a salt thereof. A method for suppressing the generation of a compound represented by general formula (2) or a salt thereof including containing a compound represented by general formula (1) or a salt thereof and a magnesium compound in an aqueous liquid formulation.

7 Claims, 2 Drawing Sheets

FIG.2

| No. | 2θ | RELATIVE INTENSITY | INTENSITY |
|---|---|---|---|
| 1 | — | vs | — |
| 2 | 9.6 | m | 872 |
| 3 | — | m | — |
| 4 | 11.6 | s | 2228 |
| 5 | — | vs | — |
| 6 | 13.5 | m | 823 |
| 7 | 14.4 | m | 1306 |
| 8 | 14.7 | s | 1913 |
| 9 | 15.7 | m | 778 |
| 10 | 15.8 | m | 940 |
| 11 | 16.4 | m | 945 |
| 12 | 16.9 | m | 712 |
| 13 | 17.1 | m | 717 |
| 14 | 17.3 | m | 1140 |
| 15 | — | vs | — |
| 16 | 18.5 | w | 435 |
| 17 | 19.3 | w | 310 |
| 18 | 19.5 | m | 528 |
| 19 | 19.7 | m | 610 |
| 20 | 19.9 | w | 302 |
| 21 | 20.2 | m | 718 |
| 22 | 21.2 | s | 1990 |
| 23 | 21.6 | m | 1335 |
| 24 | — | vs | — |
| 25 | 22.4 | m | 757 |
| 26 | 23.4 | m | 1393 |
| 27 | 23.9 | m | 852 |
| 28 | 24.2 | m | 899 |
| 29 | — | s | — |
| 30 | 25.0 | m | 1038 |
| 31 | 25.3 | w | 470 |
| 32 | 25.5 | m | 695 |
| 33 | 25.6 | m | 683 |
| 34 | 26.0 | m | 997 |
| 35 | — | s | — |
| 36 | 26.8 | m | 1677 |
| 37 | 27.3 | m | 922 |
| 38 | 27.8 | m | 715 |
| 39 | 28.3 | m | 717 |
| 40 | 29.0 | w | 395 |
| 41 | 29.5 | m | 610 |
| 42 | 30.3 | w | 330 |
| 43 | 31.6 | m | 615 |
| 44 | 32.2 | m | 863 |
| 45 | 32.5 | w | 408 |
| 46 | 32.8 | m | 843 |
| 47 | 33.1 | w | 402 |
| 48 | 33.6 | m | 835 |
| 49 | 34.0 | w | 338 |
| 50 | 34.4 | w | 355 |
| 51 | 34.8 | m | 533 |
| 52 | 35.4 | m | 510 |
| 53 | 36.1 | w | 383 |
| 54 | 36.5 | w | 453 |
| 55 | 36.8 | w | 435 |
| 56 | 39.0 | m | 625 |
| 57 | 39.3 | w | 380 |

DEFINITION
% RELATIVE INTENSITY (ri)   DEFINITION
  $50 \leq ri \leq 100$   vs (VERY STRONG)
  $20 \leq ri < 50$   s (STRONG)
  $5 \leq ri < 20$   m (MODERATE)
  $0.7 \leq ri < 5$   w (WEAK)
  $ri < 0.7$   vw (VERY WEAK)

AQUEOUS LIQUID FORMULATION

TECHNICAL FIELD

The present invention relates to an aqueous liquid formulation. More specifically, the present invention relates to an aqueous liquid formulation that contains a compound represented by general formula (1) (hereinafter, also referred to as a compound of formula (1)) or a salt thereof.

[Chemical Formula 1]

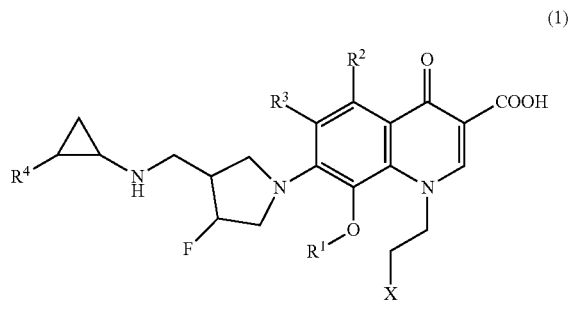

(1)

In the formula (1), $R^1$ represents an alkyl group having 1 to 3 carbon atoms which is optionally substituted with one or more substituents selected from the group consisting of a hydrogen atom, a halogen atom, an amino group, a cyano group, or a hydroxyl group, $R^2$ represents a hydrogen atom, a halogen atom, a hydroxyl group, an amino group or an alkyl group having 1 to 3 carbon atoms which is optionally substituted with one or more substituents selected from the group consisting of a hydrogen atom, a halogen atom, an amino group, a cyano group or a hydroxyl group, $R^3$ represents a hydrogen atom or a halogen atom, $R^4$ represents a hydrogen atom or a halogen atom, and X represents a halogen atom.

BACKGROUND ART

It is known that a 7-[4-substituted-3-{(cyclopropylamino)methyl}-1-pyrrolidinyl]quinolone carboxylic acid derivative not only is safe and has a strong antibacterial activity, but also exhibits a strong antibacterial activity to resistant bacteria such as methicillin-resistant *Staphylococcus aureus* (MRSA), penicillin-resistant *Streptococcus pneumoniae* (PRSP), and vancomycin-resistant *Enterococcus* (VRE) (Patent Literature 1).

An aqueous liquid formulation having a pH that is higher or lower than the physiological pH sometimes provides stimuli when administered. Hence, it is preferable to design an aqueous liquid formulation which has a pH around the physiological pH, that is, a near-neutral pH, when designing an aqueous liquid formulation such as an injectable formulation. Patent Literatures 2 to 7 disclose an aqueous liquid formulation in which a quinolone carboxylic acid derivative is contained as a principal agent and which is neutral pH. These literatures disclose a formulation in which the precipitation of the principal agent is suppressed and the principal agent is solubilized by adding polyvalent metal such as magnesium into a solution (Patent Literatures 2 to 7).

On the other hand, there is known an aqueous liquid formulation in which a solution containing a quinolone carboxylic acid derivative as a principal agent is adjusted to be slightly acidic around pH 4 thereby to improve the chemical and physical stability of the principal agent (Patent Literatures 8 to 9). Patent Literature 9 discloses a formulation provided with a lyophilized formulation containing quinolone carboxylic acid and a dilution liquid containing a polyvalent metal compound.

It is noted that the quinolone carboxylic acid derivative disclosed in Patent Literatures 2 to 9 does not have a cyclopropylaminomethyl structure.

CITATION LIST

Patent Literature

Patent Literature 1: WO2005/026147
Patent Literature 2: WO1991/009525
Patent Literature 3: WO1997/023217
Patent Literature 4: WO1999/29322
Patent Literature 5: JP1988-188626
Patent Literature 6: JP1992-230631
Patent Literature 7: JP1990-264724
Patent Literature 8: JP2004-509921
Patent Literature 9: WO2006/004028

SUMMARY OF INVENTION

Technical Problem

An object of the present invention is to provide a novel aqueous liquid formulation that contains a compound of formula (1) or a salt thereof, in which the chemical decomposition of the compound of the formula (1) or a salt thereof is suppressed.

Solution to Problem

The present inventors intensively conducted research on the preparation of the aqueous liquid formulation that contains the compound of the formula (1) or a salt thereof. As a result, they determined that the cyclopropylaminomethyl structure contained in the compound of the formula (1) is likely to be chemically decomposed, causing the generation of a compound represented by general formula (2) (hereinafter, also referred to as a "compound of formula (2)") in which a cyclopropyl group is detached:

[Chemical Formula 2]

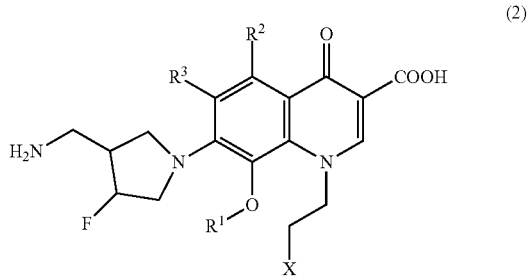

(2)

(wherein, $R^1$, $R^2$, $R^3$ and X are defined as described above).

The present invention provides: a method for suppressing generation of a compound of formula (2) or a salt thereof in an aqueous liquid formulation that contains a compound of formula (1) or a salt thereof; and an aqueous liquid formulation in which the generation of the compound of the formula (2) or a salt thereof is suppressed.

The present inventors have found out that the generation of the compound of the formula (2) or a salt thereof can be suppressed by containing the compound of the formula (1) or a salt thereof and the magnesium compound in the aqueous liquid formulation.

The present invention will be described in further detail below.

<1> A method for suppressing generation of a compound represented by general formula (2) or a salt thereof, the method including containing a compound represented by general formula (1) or a salt thereof and a magnesium compound in an aqueous liquid formulation:

[Chemical Formula 3]

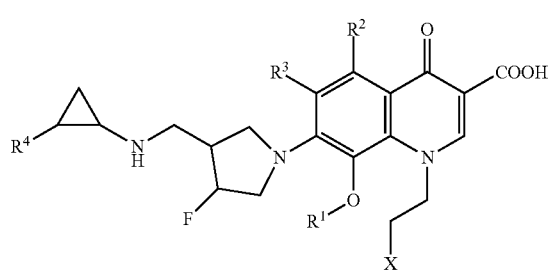

(1)

(wherein $R^2$ represents an alkyl group having 1 to 3 carbon atoms which is optionally substituted with one or more substituents selected from the group consisting of a hydrogen atom, a halogen atom, an amino group, a cyano group, or a hydroxyl group, $R^2$ represents a hydrogen atom, a halogen atom, a hydroxyl group, an amino group or an alkyl group having 1 to 3 carbon atoms which is optionally substituted with one or more substituents selected from the group consisting of a hydrogen atom, a halogen atom, an amino group, a cyano group or a hydroxyl group, $R^3$ represents a hydrogen atom or a halogen atom, $R^4$ represents a hydrogen atom or a halogen atom, and X represents a halogen atom),

[Chemical formula 4]

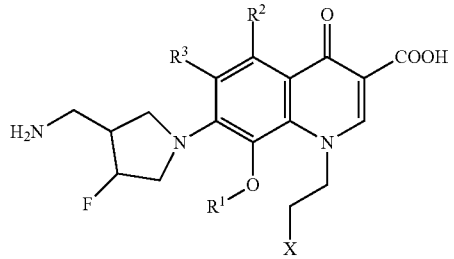

(2)

(wherein, $R^1$, $R^2$, $R^3$ and X are defined as described above).

<2> The method according to <1>, wherein a molar ratio of the magnesium compound relative to the compound represented by the general formula (1) or the salt thereof is 0.45 or more and 1.5 or less.

<3> The method according to <1> or <2>, wherein a concentration of the compound represented by the general formula (1) in the aqueous liquid formulation is less than 3 mg/mL.

<4> An aqueous liquid formulation including: a compound represented by general formula (1):

[Chemical Formula 5]

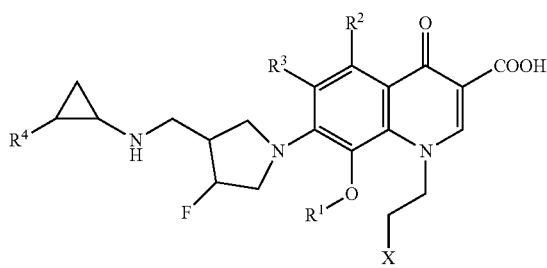

(1)

(wherein $R^1$ represents an alkyl group having 1 to 3 carbon atoms which is optionally substituted with one or more substituents selected from the group consisting of a hydrogen atom, a halogen atom, an amino group, a cyano group, or a hydroxyl group, $R^2$ represents a hydrogen atom, a halogen atom, a hydroxyl group, an amino group or an alkyl group having 1 to 3 carbon atoms which is optionally substituted with one or more substituents selected from the group consisting of a hydrogen atom, a halogen atom, an amino group, a cyano group or a hydroxyl group, $R^3$ represents a hydrogen atom or a halogen atom, $R^4$ represents a hydrogen atom or a halogen atom, and X represents a halogen atom) or a salt thereof; and a magnesium compound, wherein a concentration of the compound represented by the formula (1) is less than 3 mg/mL.

<5> The aqueous liquid formulation according to <4>, wherein a pH of the aqueous liquid formulation is 5.8 or more and 6.9 or less.

<6> The aqueous liquid formulation according to <4> or <5>, wherein a molar ratio of the magnesium compound relative to the compound represented by the general formula (1) or the salt thereof is 0.45 or more and 1.5 or less.

<7> The aqueous liquid formulation according to any one of <4> to <6>, wherein the aqueous liquid formulation is diluted with a saline solution when the aqueous liquid formulation is administered to a patient.

Advantageous Effects of Invention

According to the present invention, a novel technique with which chemical decomposition of the compound of the formula (1) or a salt thereof can be suppressed in the aqueous liquid formulation containing the compound of the formula (1) or a salt thereof can be provided.

BRIEF DESCRIPTION OF DRAWINGS

FIG. 2 is a table describing peaks having a relative intensity of 0.7 or more when the intensity of the peak at 2θ=4.9 degrees in the diffraction pattern illustrated in FIG. 1 is assumed to be 100.

DESCRIPTION OF EMBODIMENTS

Figure 1:
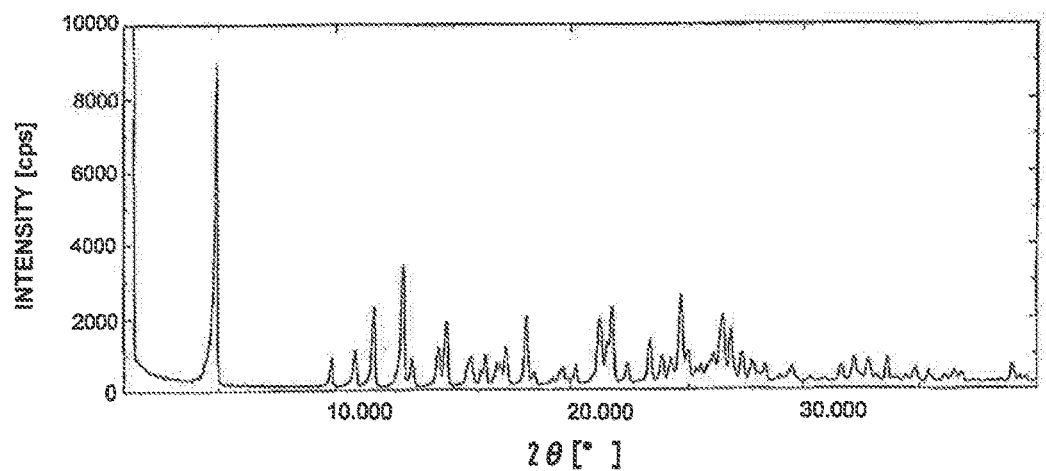
FIG. 1 illustrates a powder X-ray diffraction pattern of A-type crystals of 7-[(3S,4S)-3-{(cyclopropylamino) methyl}-4-fluoropyrrolidine-1-yl]-6-fluoro-1-(2-fluoro-ethyl)-8-methoxy-4-oxo-1,4-dihydroquinoline-3-carboxylic acid hydrochloride.

Hereinafter, an embodiment of the present invention will be described in detail. The present embodiment relates to an aqueous liquid formulation containing a compound represented by general formula (1) or a salt thereof and a magnesium compound. Generation of a compound represented by general formula (2) or a salt thereof can be suppressed by containing the compound represented by the general formula (1) or a salt thereof and the magnesium compound in the aqueous liquid formulation.

[Chemical Formula 6]

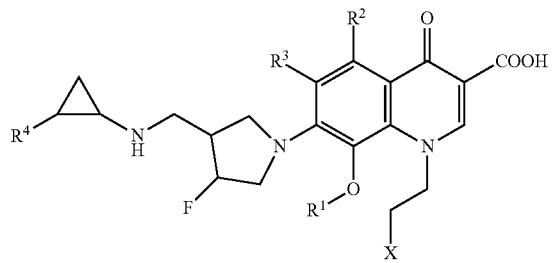

(1)

In the formula (1), $R^1$ represents an alkyl group having 1 to 3 carbon atoms which is optionally substituted with one or more substituents selected from the group consisting of a hydrogen atom, a halogen atom, an amino group, a cyano group, or a hydroxyl group, $R^2$ represents a hydrogen atom, a halogen atom, a hydroxyl group, an amino group or an alkyl group having 1 to 3 carbon atoms which is optionally substituted with one or more substituents selected from the group consisting of a hydrogen atom, a halogen atom, an amino group, a cyano group or a hydroxyl group, $R^3$ represents a hydrogen atom or a halogen atom, $R^4$ represents a hydrogen atom or a halogen atom, and X represents a halogen atom.

[Chemical Formula 7]

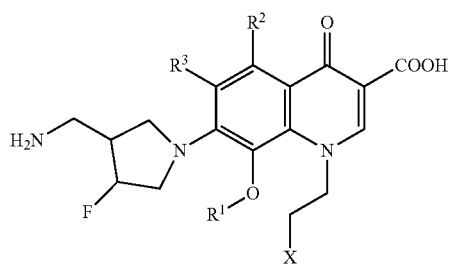

(2)

(in the formula (2), $R^1$, $R^2$, $R^3$ and X are defined as described above).

The "magnesium compound" described herein is a compound that contains magnesium. Examples of the magnesium compound may include an inorganic magnesium salt such as magnesium chloride, magnesium sulfate, magnesium nitrate, and magnesium phosphate, and an organic magnesium salt such as magnesium citrate, magnesium gluconate, magnesium acetate, and magnesium propionate. As the magnesium compound, one or more of these compounds may be used. The magnesium compound may preferably be an inorganic magnesium salt, and particularly preferably magnesium chloride.

The "aqueous liquid formulation" described herein is a formulation that contains water as base material and is in the form of liquid. Examples thereof may include an injectable formulation, an ophthalmic liquid drug, aqueous nasal drops, aqueous ear drops, and an inhalant liquid drug.

The "injectable formulation" described herein is a sterile formulation to be directly administered to body tissues and organs, such as subcutaneous or intramuscular tissues and blood vessels.

The "dilution liquid" described herein means any solvent or solution that is not harmful when administered to a patient. Examples of the dilution liquid may include water, a saline solution, a Ringer's solution, a glucose solution, a lactate Ringer's solution, an acetate Ringer's solution, a bicarbonate Ringer's solution, a maltose liquid, and a xylitol liquid. As the dilution liquid, one or a mixture of two or more of these dilution liquids may be used. As the dilution liquid, a saline solution may be particularly preferable.

The "halogen atom" described herein represents a fluorine atom, a chlorine atom, a bromine atom, or an iodine atom. Among these, a fluorine atom is preferable. The "alkyl group having 1 to 3 carbon atoms" described herein represents a methyl group, an ethyl group, a propyl group, or a 2-propyl group.

The compound represented by the general formula (1) can be manufactured by, for example, the method described in the WO2005/026147 pamphlet. The compound of the formula (1) contained in the aqueous liquid formulation according to the present embodiment may be preferably 7-[3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid, and further preferably 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid. A salt of the compound of the formula (1) is preferably used in terms of the improvement of the solubility to water.

Examples of the salt of the compound of the formula (1) may include a salt formed with an inorganic acid such as hydrochloric acid, hydrobromic acid, sulfuric acid, and phosphoric acid, a salt formed with an organic acid such as maleic acid, fumaric acid, succinic acid, malic acid, malonic acid, methanesulfonic acid, toluenesulfonic acid, benzenesulfonic acid, lactic acid, oxalic acid, acetic acid, trifluoroacetic acid, and tartaric acid, and a salt formed with metal such as sodium, potassium, magnesium, calcium, aluminum, cesium, chromium, cobalt, copper, iron, zinc, platinum, and silver. Among these salts of the compound of the formula (1), a hydrochloride may be particularly preferable from the viewpoint of stability. In particular, a hydrochloride of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid is excellent as a salt of the compound of the formula (1), because decomposition by light exposure is unlikely to occur, and chemical decomposition is unlikely to occur even when the storage under accelerated test conditions is performed.

The pH of the aqueous liquid formulation of the present embodiment is preferably 5.8 or more and 6.9 or less, in terms of the suppression of the precipitation of the compound of the formula (1) or a salt thereof during the storage of the aqueous liquid formulation. Furthermore, the aqueous liquid formulation is preferably diluted with the dilution liquid before administered to a patient. In terms of the suppression of the precipitation of the compound of the formula (1) or a salt thereof during the dilution, the pH of the aqueous liquid formulation of the present embodiment is preferably 5.8 or more and 6.5 or less.

As described above, the compound of the formula (1) or a salt thereof is likely to be chemically decomposed in the aqueous liquid formulation to generate the compound of the formula (2) or a salt thereof. In terms of further suppression of the generation of this compound of the formula (2) or a salt thereof, the concentration of the compound represented by the formula (1) in the aqueous liquid formulation is preferably less than 3 mg/mL, more preferably 2 mg/mL or less, further preferably 1.5 mg/mL or less, particularly preferably 1.0 mg/mL or less, and still further preferably 0.5 mg/mL or less.

The above-described "concentration of the compound represented by formula (1) in the aqueous liquid formulation" is a value obtained by dividing the weight (mg) of the compound of the formula (1) contained in the aqueous liquid formulation by the solvent amount (mL) of the liquid formulation. It is noted that when a salt of the compound of the formula (1) is used, the above-described "concentration of the compound represented by formula (1) in the aqueous liquid formulation" is a value obtained by dividing the value (mg) of the weight of the compound of the formula (1) converted from the weight (mg) of the salt of the compound of the formula (1), by the solvent amount (mL).

The use amount of the magnesium compound is not particularly limited. In terms of the improved solubility of the compound of the formula (1) or a salt thereof to water for suppressing the precipitation of the compound of the formula (1) or a salt thereof and the generation of the compound of the formula (2), the molar ratio of the magnesium compound relative to the compound of the formula (1) or a salt thereof may be preferably 0.35 or more, more preferably 0.40 or more, further more preferably 0.45 or more, and still further more preferably 0.70 or more. The "molar ratio of the magnesium compound relative to the compound of the formula (1) or a salt thereof" is a value represented by the formula below:

"molar ratio of magnesium compound relative to compound of the formula (1) or salt thereof"=number of moles (mol) of magnesium compound contained in aqueous liquid formulation/number of moles (mol) of compound of the formula (1) or salt thereof contained in aqueous liquid formulation.

Also, in consideration of the administration amount per day of the magnesium compound, the "molar ratio of magnesium compound relative to compound of the formula (1) or a salt thereof" may be preferably 3.0 or less, more preferably 1.5 or less, and further more preferably 1.1 or less.

The "molar ratio of magnesium compound relative to compound of the formula (1) or a salt thereof" is particularly preferably 0.45 or more and 1.5 or less, and further more preferably 0.70 or more and 1.1 or less.

The "pH adjuster" described herein includes an acid, a base, or a buffer. Examples of the pH adjuster may include hydrochloric acid, sulfuric acid, adipic acid or a salt thereof, citric acid or a salt thereof, gluconic acid or a salt thereof, succinic acid or a salt thereof, ascorbic acid or a salt thereof, glacial acetic acid or a salt thereof, acetic acid or a salt thereof, tartaric acid or a salt thereof, fumaric acid or a salt thereof, maleic acid or a salt thereof, lactic acid or a salt thereof, malic acid or a salt thereof, phosphoric acid or a salt thereof, glycine, sodium hydrogen carbonate, sodium carbonate, sodium hydroxide, and magnesium hydroxide. One or more of these pH adjusters may be used. As the pH adjuster, hydrochloric acid and sodium hydroxide may be preferable, and hydrochloric acid and sodium hydroxide may be more preferable. With the pH adjuster, the pH of the aqueous liquid formulation can be adjusted within an appropriate range.

The present invention will be described in further detail below by illustrating a general manufacturing method of the aqueous liquid formulation of the present embodiment. However, this does not limit the scope of the present invention.

The content of the compound represented by the general formula (1) in the aqueous liquid formulation is preferably 500 mg or less, more preferably 10 mg or more and 450 mg or less, further preferably 20 mg or more and 400 mg or less, further more preferably 30 mg or more and 200 mg or less, and particularly preferably 50 mg or more and 160 mg or less. The content of the compound represented by the general formula (1) when a salt of the compound represented by the general formula (1) is contained means a value (mg) obtained by converting the weight (mg) of the salt of the compound represented by the general formula (1) into the weight of the compound represented by the general formula (1).

(General Manufacturing Method 1)

A magnesium compound is dissolved in a physiologically acceptable carrier such as water, a saline solution, a Ringer's solution, a glucose solution, a lactate Ringer's solution, an acetate Ringer's solution, a bicarbonate Ringer's solution, a maltose liquid, and a xylitol liquid. To the obtained solution, a pH adjuster is added. Thereafter, the compound of the formula (1) or a salt thereof is added. (Here, the molar ratio of the magnesium compound relative to the compound of the formula (1) or a salt thereof is preferably 0.35 or more, and further preferably 0.45 or more and 1.5 or less.) The resultant solution is stirred so that the compound of the formula (1) or a salt thereof is dissolved. Furthermore, the pH of the solution may be adjusted by the process of adding a pH adjuster to the solution. Also, the amount of the solution may be adjusted by the process of adding a physiologically acceptable carrier to the solution.

According to the above-described operation, there can be obtained the aqueous liquid formulation containing the compound of the formula (1) or a salt thereof and the magnesium compound, in which the generation of the compound of the formula (2) is suppressed.

Although the present invention will be described in further detail with reference to examples below, these examples do not limit the scope of the present invention.

In Examples below, the NMR spectrum was measured using a JNM-EX400 type nuclear magnetic resonance apparatus manufactured by JEOL Ltd. with tetramethyl silane (TMS) as an internal standard. The MS spectrum was measured using JMS-T100LP type and JMS-SX102A type mass spectrometers manufactured by JEOL Ltd. The elemental analysis was performed using a CHN CORDER MT-6 elemental analyzer manufactured by Yanaco Bunseki Kogyo Co.

Also, powder X-ray diffraction was performed using RINT2200 manufactured by Rigaku Corporation. Copper radiation was used as radiation. The measurement condition was a tube current of 36 mA, a tube voltage of 40 kV, a divergence slit of 1 degree, a scattering slit of 1 degree, a receiving slit of 0.15 mm, a scan range of 1 to 40 degrees (2θ), and a scan rate per minute of 2 degrees (2θ).

Reference Example 1

Bis(acetato-O)-{6,7-difluoro-1-(2-fluoroethyl)-8-methoxy-4-oxo-1,4-dihydroquinoline-3-carboxylato-$O^3,O^4$}boron Under nitrogen atmosphere, 103 g (1.67 mol) of boric acid (for the formation of a catalyst) was added to 21.4 L (225 mol) of anhydrous acetic acid. The mixture was heated and stirred at 70.0 to 76.9° C. for 30 minutes (stirring speed: 69.5 rpm). The mixed liquid was cooled to an internal temperature of 24.6° C. Thereafter, 1.01 kg (16.3 mol) of boric acid (first portion) was added to the mixed liquid, and the mixed liquid was stirred at 24.6 to 27.4° C. for 30 minutes. Then, 1.01 kg (16.3 mol) of boric acid (second portion) was added to the mixed liquid, and the mixed liquid was stirred at 24.7 to 27.5° C. for 30 minutes. Next, 1.01 kg (16.3 mol) of boric acid (third portion) was added to the mixed liquid, and the mixed liquid was stirred at 24.7 to 27.7° C. for 30 minutes. Subsequently, 1.01 kg (16.3 mol) of boric acid (forth portion) was added to the mixed liquid, and the mixed liquid was stirred at 25.4 to 29.4° C. for 30 minutes. Furthermore, the mixed liquid was stirred at 50.0 to 56.9° C. for 30 minutes to obtain a boric acid triacetate adjusting liquid.

To the adjusting liquid, 5.50 kg (16.7 mol) of 6,7-difluoro-1-(2-fluoroethyl)-8-methoxy-4-oxo-1,4-dihydroquinoline-3-carboxylic acid ethyl ester was added, and the adjusting liquid was stirred at 54.7 to 56.9° C. for 3 hours. The adjusting liquid was then cooled to 30.0° C., and allowed to stand at room temperature overnight. The resultant adjusting liquid was heated to 58.6° C. to dissolve the precipitate. Then, 16.5 L of acetone was added to the adjusting liquid to obtain a reaction liquid (1).

Under nitrogen atmosphere, a mixed liquid of 193 L of water and 33.7 L (555 mol) of aqueous ammonia (28%) was cooled to −0.6° C. To the mixed liquid, the aforementioned reaction liquid (1) was added, and the vessel for the reaction liquid (1) was washed with 11.0 L of acetone. Thus, the reaction liquid (2) was obtained. The reaction liquid (2) was cooled to 15.0° C., and thereafter stirred at 4.3 to 15.0° C. for one hour. Precipitated crystals were separated by filtration, and washed with 55.0 L of water. Thus, 14.1 kg of wet crude crystals were obtained. The obtained wet crude crystals were dried under reduced pressure at a preset temperature of 65.0° C. for approximately 22 hours to obtain 6.93 kg of crude crystals (yield: 96.7%).

To the obtained crude crystals, 34.7 L of acetone was added under nitrogen atmosphere to prepare a mixed liquid, and the mixed liquid was heated (hot water preset temperature: 57.0° C.) to dissolve the crude crystal. During the heating, 69.3 L of diisopropyl ether was dropped to the mixed liquid until crystallization occurred (dropping amount: 12.0 L). After crystallization was confirmed, the mixed liquid was stirred at 48.3 to 51.7° C. for 15 minutes. Then, the remaining diisopropyl ether was dropped to the mixed liquid, and the mixed liquid was stirred at 45.8 to 49.7° C. for 15 minutes. The mixed liquid was cooled to 15° C., and thereafter stirred at 6.5 to 15.0° C. for 30 minutes. The precipitated crystals were separated by filtration, and washed with 6.93 L of acetone and 13.9 L of diisopropyl ether. Thus, 7.41 kg of wet crystals were obtained. The obtained wet crystals were dried under reduced pressure at a preset temperature of 65.0° C. for approximately 20 hours to obtain 6.47 kg of bis(acetato-O)-{6,7-difluoro-1-(2-fluoroethyl)-8-methoxy-4-oxo-1,4-dihydroquinoline-3-carboxylato-$O^3,O^4$}boron (yield: 90.30).

Elemental Analysis Value (%): as $C_{17}H_{15}BF_3NO_8$
Calcd.: C, 47.58; H, 3.52; N, 3.26.
Measured: C, 47.41; H, 3.41; N, 3.20.
$^1$H-NMR (CDCl$_3$, 400 MHz) δ: 2.04 (6H, s), 4.21 (3H, d, J=2.9 Hz), 4.88 (2H, dt, J=47.0, 4.4 Hz), 5.21 (2H, dt, J=24.9, 3.9 Hz), 8.17 (1H, t, J=8.8 Hz), 9.10 (1H, s).

ESI MS (positive) m/z: 430 (M+H)$^+$.

Reference Example 2

7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid hydrochloride Under nitrogen atmosphere, 3.56 kg (15.4 mol) of (3R,4S)-3-cyclopropylaminomethyl-4-fluoropyrrolidine, 11.7 L (84.2 mol) of triethylamine, and 30.0 L of dimethylsulfoxide was mixed to obtain a reaction liquid. The reaction liquid was stirred at 23.0 to 26.3° C. for 15 minutes. At 23.0 to 26.3° C., 6.00 kg (14.0 mol) of bis(acetato-O)-{6,7-difluoro-1-(2-fluoroethyl)-8-methoxy-4-oxo-1,4-dihydroquinoline-3-carboxylato-$O^3,O^4$}boron was added to the reaction liquid. The reaction liquid was stirred at 23.7 to 26.3° C. for 2 hours. To the reaction liquid, 120 L of ethyl acetate was added, and 120 L of water was further added. Thereafter, a solution of 960 g (an amount for obtaining 2 mol/L) of sodium hydroxide and 12.0 L of water was added. After the mixture was stirred for 5 minutes, an aqueous layer was separated. To the aqueous layer, 120 L of ethyl acetate was added. The mixture was stirred for 5 minutes. Then, an ethyl acetate layer was separated.

The portions of the ethyl acetate layer were combined, and 120 L of water was added. The mixture was stirred for 5 minutes, and left to stand. Then, an aqueous layer was removed. The ethyl acetate layer was evaporated under reduced pressure. The obtained residue was dissolved in 60.0 L of 2-propanol, and the solution was allowed to stand at room temperature overnight. A solution of 5.24 L (62.9 mol) of hydrochloric acid and 26.2 L (an amount for obtaining 2 mol/L) of water was added to the obtained 2-propanol solution. The mixed liquid was stirred at 28.2 to 30.0° C. for 30 minutes. The obtained mixed liquid was heated at an outer temperature of 55.0° C. After dissolution (dissolution was confirmed at 47.1°), the mixed liquid was cooled, resulting in crystallization. The mixed liquid was stirred at 39.9 to 41.0° C. for 30 minutes. After cooling (approximately temperature setting: 7.0° C. until 20° C. and −10.0° C. below 20.0° C.), the mixed liquid was stirred at 2.2 to 10.0° C. for one hour. Precipitated crystals were collected by filtration, and washed with 60 L of 2-propanol to obtain 9.57 kg of wet crude crystals of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid hydrochloride.

Reference Example 3

A-type crystals of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid hydrochloride (compound (1))

To a mixed solvent of 60 L of ethanol and 10.8 L of purified water, 9.57 kg of wet crude crystals of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid hydrochloride was added, and dissolved by heating. This solution was filtered, and the vessel for the solution was washed with a mixed solvent of 24.0 L of ethanol and 1.20 L of purified water. The dissolution was confirmed, and 96.0 L of heated ethanol (99.5 was added to the solution at 71.2 to 72.6° C. This solution was cooled (hot water preset temperature: 60.0° C.), and crystallization was confirmed (crystallization temperature: 61.5° C.). Thereafter, the obtained product was stirred at 59.4 to 61.5° C. for 30 minutes, and cooled in a stepwise manner (Hot water temperature setting: 40° C. until 50° C., 30° C. until 40° C., 20° C. until 30° C., 7.0° C. until 20.0° C., −10° C. until 15.0° C., and then left to stand), and stirred at 4.8 to 10.0° C. for one hour. Precipitated crystals were separated by filtration, and washed with 30.0 L of ethanol to obtain 5.25 kg of wet crystals of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid hydrochloride. The obtained wet crystals were dried under reduced pressure at a preset temperature of 50.0° C. for approximately 13 hours to obtain 4.83 kg of the compound (1) (yield: 72.6%).

The result of the powder X-ray diffraction of the compound (1) based on WO2013/069297 is shown in FIGS. 1 and 2. As understood from FIGS. 1 and 2, peaks are observed at 4.9 degrees, 9.8 degrees, 10.8 degrees, 12.9 degrees, 14.7 degrees, 18.2 degrees, 21.7 degrees, 23.4 degrees, 24.7 degrees, and 26.4 degrees, and characteristic peaks can be confirmed at 4.9 degrees, 10.8 degrees, 12.9 degrees, 18.2 degrees, 21.7 degrees, 24.7 degrees, and 26.4 degrees. Particularly characteristic peaks can be confirmed at 10.8 degrees, 12.9 degrees, and 24.7 degrees.

Elemental Analysis Value (%): as $C_{21}H_{24}F_3N_3O_4HCl$
Calcd.: C, 53.00; H, 5.30; N, 8.83.
Measured: C, 53.04; H, 5.18; N, 8.83.
$^1$H NMR (DMSO-$d_6$, 400 MHz) δ (ppm): 0.77-0.81 (2H, m), 0.95-1.06 (2H, m), 2.80-2.90 (2H, m), 3.21-3.24 (1H, m), 3.35-3.39 (1H, m), 3.57 (3H, s), 3.65-3.78 (3H, m), 4.13 (1H, dd, J=41.8, 13.1 Hz), 4.64-4.97 (3H, m), 5.14 (1H, dd, J=32.7, 15.6 Hz), 5.50 (1H, d, J=53.7 Hz), 7.80 (1H, d, J=13.7 Hz), 8.86 (1H, s), 9.44 (2H, brs), 15.11 (1H, brs).
ESI MS (positive) m/z: 440 (M+H)$^+$.

Relationship Between Magnesium Chloride and Stability

Example 1

According to the formulation shown in Table 1, 920 mg of magnesium chloride hexahydrate was dissolved in water for injection. To the solution, 8 mL of 0.1 mol/L aqueous sodium hydroxide solution was added. Thereafter, 4.332 g of the compound (1) was added to the obtained solution and dissolved. To this solution, 0.1 mol/L hydrochloric acid and 0.1 mol/L aqueous sodium hydroxide solution were added to adjust the pH to 6.0. To this solution, water for injection was added so that the total amount became 100 mL.

Example 2

According to the formulation shown in Table 1, 1.39 g of magnesium chloride hexahydrate was dissolved in water for injection. To the solution, 8 mL of 0.1 mol/L aqueous sodium hydroxide solution was added. Thereafter, 4.332 g of the compound (1) was added to the obtained solution and dissolved. To this solution, 0.1 mol/L hydrochloric acid and 0.1 mol/L aqueous sodium hydroxide solution were added to adjust the pH to 6.0. To this solution, water for injection was added so that the total amount became 100 mL.

Example 3

According to the formulation shown in Table 1, 1.85 g of magnesium chloride hexahydrate was dissolved in water for injection. To the solution, 8 mL of 0.1 mol/L aqueous sodium hydroxide solution was added. Thereafter, 4.332 g of the compound (1) was added to the obtained solution and dissolved. To this solution, 0.1 mol/L hydrochloric acid and 0.1 mol/L aqueous sodium hydroxide solution were added to adjust the pH to 6.0. To this solution, water for injection was added so that the total amount became 100 mL.

It is noted that as water for injection in Examples 1 to 3, the water for injection defined in the Japanese Pharmacopoeia 16th Edition was used.

TABLE 1

| Components | Prescription | | |
| --- | --- | --- | --- |
| | Example 1 | Example 2 | Example 3 |
| Compound (1) | 4.332 g | 4.332 g | 4.332 g |
| Magnesium chloride hexahydrate | 920 mg | 1.39 g | 1.85 g |
| 0.1 mol/L hydrochloric acid | As needed | As needed | As needed |
| 0.1 mol/L aqueous sodium hydroxide solution | As needed | As needed | As needed |
| Water for injection | As needed | As needed | As needed |
| (Total) | 100 mL | 100 mL | 100 mL |
| (pH) | 6.0 | 6.0 | 6.0 |

Test Example 1

The aqueous liquid formulation prepared in each of Examples 1 to 3 was stored in a constant-temperature bath at 40±2° C. for 4 weeks. After the storage, the content of 7-{(3S,4S)-3-aminomethyl-4-fluoropyrrolidine-1-yl}-6-fluoro-1-(2-fluoroethyl)-8-methoxy-4-oxo-1,4-dihydroquinoline-3-carboxylic acid (compound (2)) and the content of the compound (1) in each aqueous liquid formulation were measured by liquid chromatography (Alliance system, manufactured by Waters Company).

(Condition of Measurement by Liquid Chromatography)

Separation column: a stainless tube having an inner diameter of 4.6 mm and a length of 15 cm was filled with octadecyl silylated silica gel for liquid chromatography with the size of 3 μm.

Liquid A: a 1000 mL solution obtained by dissolving 2.16 g of sodium 1-octanesulfonate in diluted phosphoric acid (from 1 to 1000)

Liquid B: methanol for liquid chromatography

Flow velocity: 1.0 mL

Detector: UV absorptiometer (measurement wavelength: 294 nm)

Retention time of compound (2) relative to retention time of compound (1): 0.69

Liquid sending: the mixing ratio of liquid A and liquid B is shown in Table 2.

TABLE 2

| Mixing ratio between liquid A and liquid B | | |
| --- | --- | --- |
| Analysis time (minute) | Liquid A | Liquid B |
| 0~32 | 56 | 44 |
| 32~50 | 56→30 | 44→70 |
| 50~60 | 30 | 70 |

TABLE 3

Purity test result of injectable formulation

| | Components | Example 1 | Example 2 | Example 3 |
|---|---|---|---|---|
| | Molar ratio of magnesium compound to compound (1) | 0.50 | 0.75 | 1.0 |
| Content rate (%) of compound (2) | Before storage | 0.02 | 0.00 | 0.00 |
| | After storage at 40° C. for 4 weeks | 0.74 | 0.44 | 0.35 |

The content rate of the compound (2) is shown in Table 3 as the percentage of the content of the compound (2) relative to the content of the compound (1) (hereinafter, also referred to as the "content rate of the compound (2)").

As apparent from the results in Table 3, the generated amount of the compound (2) could be further suppressed by increasing the amount of magnesium chloride contained in the aqueous liquid formulation to increase the molar ratio of the magnesium compound relative to the compound (1).

Relationship Between Concentration and Stability

Example 4

According to the formulation shown in Table 4, 54.1 mg of the compound (1) was added in purified water, and 11.5 mg of magnesium chloride hexahydrate was added. To the solution, 1 mol/L sodium hydroxide was added to adjust the pH to 6.2 for dissolution. To this solution, 1 mol/L hydrochloric acid and 1 mol/L sodium hydroxide solution were added to adjust the pH to 6.2. To this solution, water for injection was added so that the total amount became 100 mL. As a result, an aqueous liquid formulation containing the compound (1) with a concentration of 0.5 mg/mL was obtained.

Example 5

An aqueous liquid formulation in which the concentration of the compound (1) is 4 mg/mL was obtained by the same operation as that in Example 4, except that 433 mg of the compound (1) and 92 mg of magnesium chloride hexahydrate were used.

Example 6

An aqueous liquid formulation in which the concentration of the compound (1) is 8 mg/mL was obtained by the same operation as that in Example 4, except that 866 mg of the compound (1) and 184 mg of magnesium chloride hexahydrate were used.

TABLE 4

| | Prescription | | |
|---|---|---|---|
| Components | Example 4 | Example 5 | Example 6 |
| Compound (1) | 54.1 mg | 433 mg | 866 mg |
| Magnesium chloride hexahydrate | 11.5 mg | 92 mg | 184 mg |
| 0.1 mol/L hydrochloric acid | As needed | As needed | As needed |
| 0.1 mol/L aqueous sodium hydroxide solution | As needed | As needed | As needed |
| Purified water | As needed | As needed | As needed |
| (Total) | 100 mL | 100 mL | 100 mL |
| Concentration of compound (1) | 0.5 mg/mL | 4 mg/mL | 8 mg/mL |
| Molar ratio of magnesium compound to compound (1) | 0.5 | 0.5 | 0.5 |

Test Example 2

The aqueous liquid formulation prepared in each of Examples 4 to 6 was stored in a constant-temperature bath at 25±2° C. for 24 months. The content of 7-{(3S,4S)-3-aminomethyl-4-fluoropyrrolidine-1-yl}-6-fluoro-1-(2-fluoroethyl)-8-methoxy-4-oxo-1,4-dihydroquinoline-3-carboxylic acid (the compound (2)) and the content of the compound (1) were measured by liquid chromatography (Alliance system, manufactured by Waters Company), every 3 months until 6 months after the storage started, and every 6 months thereafter. The measurement by liquid chromatography was performed under the same measurement condition of Test Example 1.

TABLE 5

Purity test result of injectable formulation

| | Concentration of compound (1) | When started | 3 months | 6 months | 12 months | 18 months | 24 months |
|---|---|---|---|---|---|---|---|
| Example 4 | 0.5 mg/mL | <0.05 | 0.05 | 0.08 | 0.15 | 0.21 | 0.27 |
| Example 5 | 4 mg/mL | <0.05 | 0.18 | 0.33 | 0.59 | 0.89 | 1.28 |
| Example 6 | 8 mg/mL | <0.05 | 0.24 | 0.45 | 0.76 | 1.2 | 1.56 |

From the measured contents of the compound (1) and the compound (2), the content rate (%) of the compound (2) in the aqueous liquid formulation according to each of Examples 4 to 6 was calculated when the storage started, and after 3 months, 6 months, 12 months, 18 months, and 24 months of the storage. The results are shown in Table 5. As apparent from the results in Table 5, as the concentration of the compound (1) was lower, the generated amount of the compound (2) could be further suppressed.

Example 7

According to the formulation shown in Table 6, 108 mg of the compound (1) and 23 mg of magnesium chloride hexahydrate were added to and dissolved in purified water. To the solution, 193 µL of 1 mol/L sodium hydroxide and 900 mg of sodium chloride were added and dissolved.

Furthermore, purified water was added so that the total amount became 100 mL. Thus, an aqueous liquid formulation in which the concentration of the compound (1) is 1 mg/mL was obtained.

Example 8

According to the formulation shown in Table 6, 433 mg of the compound (1) and 92 mg of magnesium chloride hexahydrate were added to and dissolved in purified water. To the solution, 774 μL of 1 mol/L sodium hydroxide and 901 mg of sodium chloride were added and dissolved. Furthermore, purified water was added so that the total amount became 100 mL. Thus, an aqueous liquid formulation in which the concentration of the compound (1) is 4 mg/mL was obtained.

Example 9

According to the formulation shown in Table 6, 108 mg of the compound (1) and 23 mg of magnesium chloride hexahydrate were added to and dissolved in purified water. To the solution, 213 μL of 1 mol/L sodium hydroxide and 45 mg of sodium chloride were added and dissolved. Furthermore, purified water was added so that the total amount became 5 mL. Thus, an aqueous liquid formulation in which the concentration of the compound (1) is 20 mg/mL was obtained.

TABLE 6

| | Prescription | | |
|---|---|---|---|
| Components | Example 7 | Example 8 | Example 9 |
| Compound (1) | 108 mg | 433 mg | 108 mg |
| Magnesium chloride hexahydrate | 23 mg | 92 mg | 23 mg |
| 1 mol/L aqueous sodium hydroxide solution | 193 μL | 774 μL | 213 μL |
| Sodium chloride | 900 mg | 901 mg | 45 mg |
| Purified water | As needed | As needed | As needed |
| (Total) | 100 mL | 100 mL | 5 mL |
| Concentration of compound (1) | 1 mg/mL | 4 mg/mL | 20 mg/mL |
| Molar ratio of magnesium compound to compound (1) | 0.5 | 0.5 | 0.5 |

Test Example 3

The aqueous liquid formulation prepared in each of Examples 7 to 9 was stored in a constant-temperature bath at 40±2° C. for 4 weeks. Then, the content of 7-{(3S,4S)-3-aminomethyl-4-fluoropyrrolidine-1-yl}-6-fluoro-1-(2-fluoroethyl)-8-methoxy-4-oxo-1,4-dihydroquinoline-3-carboxylic acid (the compound (2)) and the content of the compound (1) were measured by liquid chromatography (Alliance system, manufactured by Waters Company), every week until 2 weeks after the storage started, and every 2 weeks thereafter.
(Condition of Measurement by Liquid Chromatography)
Separation column: A stainless tube having an inner diameter of 4.6 mm and a length of 15 cm was filled with octadecyl silylated silica gel for liquid chromatography with the size of 5 μm.
Liquid A: diluted phosphoric acid (from 1 to 1000)
Liquid B: methanol for liquid chromatography
Flow velocity: 1.0 mL/min
Detector: UV absorptiometer (measurement wavelength: 294 nm)
Retention time of compound (2) relative to retention time of compound (1): 0.63
Liquid sending: the mixing ratio of liquid A and liquid B is shown in Table 7.

TABLE 7

| | Mixing ratio between liquid A and liquid B | |
|---|---|---|
| Analysis time (minute) | Liquid A | Liquid B |
| 0~10 | 65→70 | 35→30 |
| 10~20 | 70→65 | 30→35 |
| 20~40 | 65→20 | 35→80 |
| 40~45 | 20 | 80 |

TABLE 8

| | Purity test result of injectable formulation | | | |
|---|---|---|---|---|
| | Concentration of compound (1) | When started | 1 week | 2 weeks | 4 weeks |
| Example 7 | 1 mg/mL | 0.01 | 0.07 | 0.11 | 0.23 |
| Example 8 | 4 mg/mL | 0.01 | 0.10 | 0.17 | 0.35 |
| Example 9 | 20 mg/mL | 0.01 | 0.10 | 0.21 | — |

From the measured contents of the compound (1) and the compound (2), the content rate (%) of the compound (2) in the aqueous liquid formulation according to each of Examples 7 to 9 was calculated when the storage started, and after 1 week, 2 weeks, and 4 weeks of the storage. The results are shown in Table 8. As apparent from the results in Table 8, as the concentration of the compound (1) was lower, the generated amount of the compound (2) could be further suppressed.

INDUSTRIAL APPLICABILITY

An aqueous liquid formulation that contains the compound of the formula (1) or a salt thereof and that has an excellent antibacterial activity against Gram-positive bacteria and Gram-negative bacteria is provided. The aqueous liquid formulation according to the present invention can suppress the generation of the compound of the formula (2) or a salt thereof, and is industrially useful.

The invention claimed is:
1. A method for suppressing generation of 7-{(3S,4S)-3-aminomethyl-4-fluoropyrrolidine-1-yl}-6-fluoro-1-(2-fluoroethyl)-8-methoxy-4-oxo-1,4-dihydroquinoline-3-carboxylic acid or a salt thereof, the method comprising containing 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a salt thereof and a magnesium compound in an aqueous liquid formulation.
2. The method according to claim 1, wherein a molar ratio of the magnesium compound relative to the 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or the salt thereof is 0.45 or more and 1.5 or less.
3. The method according to claim 1, wherein a concentration of the 7-[(3 S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid in the aqueous liquid formulation is less than 3 mg/mL.

4. An aqueous liquid formulation comprising: 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a salt thereof; and a magnesium compound, wherein a concentration of the 7-[(3S,4 S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid is less than 3 mg/mL.

5. The aqueous liquid formulation according to claim 4, wherein a pH of the aqueous liquid formulation is 5.8 or more and 6.9 or less.

6. The aqueous liquid formulation according to claim 4, wherein a molar ratio of the magnesium compound relative to the 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic or the salt thereof is 0.45 or more and 1.5 or less.

7. The aqueous liquid formulation according to claim 4, wherein the aqueous liquid formulation is diluted with a saline solution when the aqueous liquid formulation is administered to a patient.

\* \* \* \* \*